Figure 1:
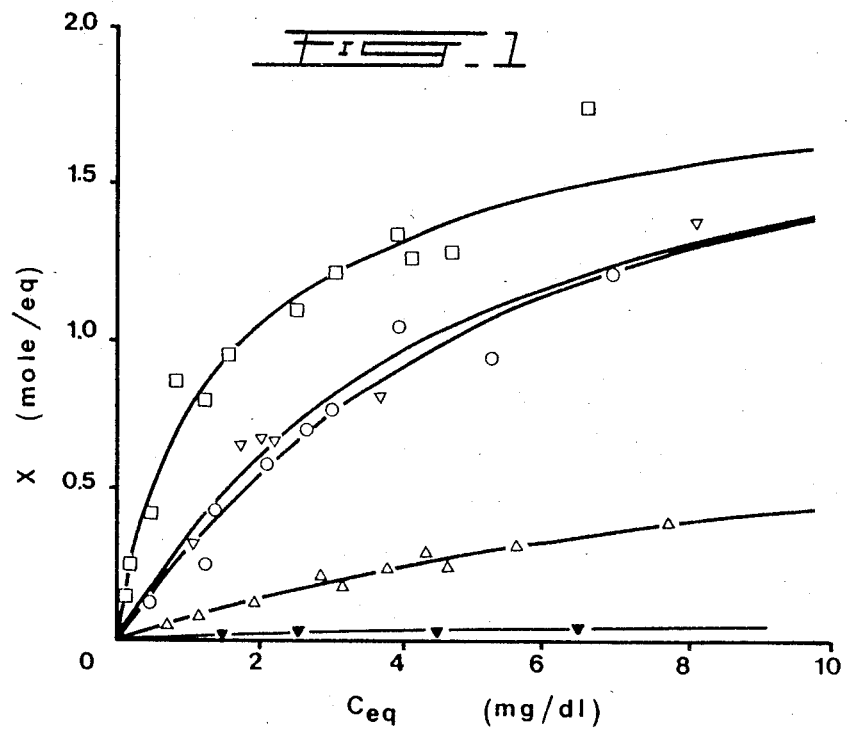

United States Patent [19]

St-Pierre et al.

[11] Patent Number: 4,593,073

[45] Date of Patent: Jun. 3, 1986

[54] POLYMER RESINS WITH AMINO ACID CONTAINING PENDANTS FOR SORPTION OF BILE PIGMENTS AND BILE ACIDS

[75] Inventors: Leon E. St-Pierre, Frelighsburg; G. Ronald Brown, Dollard des Ormeaux; Dominique S. Henning, St-Hubert; Marlene Bouvier, Montreal, all of Canada

[73] Assignee: The Royal Institution for the Advancement of Learing (McGill Univ.), Canada

[21] Appl. No.: 726,312

[22] Filed: Apr. 23, 1985

[51] Int. Cl.[4] ............................................. C08F 8/32
[52] U.S. Cl. .................................. 525/328.4; 530/815; 424/78; 424/80; 525/328.5; 525/381; 525/382
[58] Field of Search ............................ 524/17, 20, 21; 424/381, 382, 328.4, 328.5; 260/112 R; 424/78, 81

[56] References Cited

U.S. PATENT DOCUMENTS

| | | | |
|---|---|---|---|
| 4,233,287 | 11/1980 | Heusser | 424/81 |
| 4,246,351 | 1/1981 | Miyake | 524/17 |
| 4,258,151 | 3/1981 | Goldstein | 525/381 |
| 4,258,152 | 3/1981 | Goldstein | 525/381 |

*Primary Examiner*—Paul R. Michl
*Attorney, Agent, or Firm*—Oblon, Fisher, Spivak, McClelland & Maier

[57] ABSTRACT

The invention is concerned with a novel polymer addition product comprising a hydrophilic polymer backbone having a molecular weight of at least about 5,000 and to which are attached amino acid containing pendants, the pendants containing at least one arginine or lysine amino acid. The polymeric compounds of the invention are highly efficient adsorbents for bilirubin and other bile pigments, as well as for bile acids such as cholic acid.

20 Claims, 2 Drawing Figures

POLYMER RESINS WITH AMINO ACID CONTAINING PENDANTS FOR SORPTION OF BILE PIGMENTS AND BILE ACIDS

The present invention relates to novel polymeric compounds which are useful as adsorbents for bile pigments and bile acids. More particularly, the invention is directed toward the treatment of hyperbilirubinemia by adsorption of bilirubin from blood plasma or from the gastrointestinal tract.

Bilirubin, a bile pigment produced in the blood by degradation of hemoglobin, is normally conjugated with glucuronic acid in the liver, then metabolized to urobilinogen by bacterial flora in the intestines and excreted. Transport to the liver requires the formation of a complex with albumin. When complexation or conjugation is incomplete, either because of an albumin deficiency or a defect in the conjunction mechanism, the level of free bilirubin in the blood rises, causing hyperbilirubinemia. The free bilirubin diffuses into the tissues causing severe illness, e.g., jaundice and kernecticus, which may result in brain damage or death. This ailment is particularly common in newborn children and in eastern countries may affect as many as 30% of all newborns.

One possible method for the treatment of hyperbilirubinemia is adsorption of bilirubin onto an ingested adsorbent so that removal occurs in the gastrointestinal tract, thus preventing the re-absorption of bilirubin into the cardio-vascular system. Various degrees of success have been reported for the use of charcoal, agar and cholestyramine (an anion exchange resin containing quaternary ammonium groups which are attached to a styrene-divinylbenzene copolymer) as adsorbents. However, the sand-like nature of cholestyramine makes it a very uncomfortable medicine to ingest. On the other hand, it appears that many factors such as gestational age, birth weight, feeding methods and the time at which the treatment is started, greatly influence the bilirubin uptake by adsorbents in the gastrointestinal tract of newborn infants. For example, charcoal, if administered to newborns prior to 4 hours after birth, facilitates the elimination of bilirubin; however, if administered 12 hours after birth, it has no effect. Conflicting reports also exist concerning the efficiency of agar as an adsorbent for bilirubin removal from the gastrointestinal tract. Ingestion of a soluble polymer, polyvinylpyrrolidone, which can form complex with bilirubin before it is eliminated, was proposed as a possible adsorbent. When applied to Gunn rats, treatment with polyvinylpyrrolidone reportedly gave better results than does cholestyramine. However, when it was applied to newborn infants during the first 8 days of their life, the difference in bilirubin concentration between polyvinylpyrrolidone treated and control groups was significant only during the second and third days.

Physiological factors seem to be of lesser importance when adsorption of bilirubin occurs during perfusion of blood through a column packed with an adsorbent. Since plasma contains a higher concentration of bilirubin than does the gastrointestinal tract, hemoperfusion should be more efficient than the ingestion of an adsorbent. Charcoal is one of the adsorbents that has been used in hemoperfusion systems. However, there is disagreement concerning the efficiency of charcoal in removing bilirubin, with some authors reporting good adsorption while others report adsorption to be low or non-existent. Even if charcoal adsorbs bilirubin, it has the disadvantage of non-selectively adsorbing a wide variety of substances. Another major drawback associated with hemoperfusion through charcoal is the loss of platelets by adsorption. Several methods, including microencapsulation in albumin-cellulose nitrate membrane, coating with a thin polymer membrane made of polyhydroxyethylmethacrylate, have been used to improve the biocompatibility of charcoal. Polymer coating reduces the amount of adsorption while coating with albumin increases it. Nonetheless, it appears that hemoperfusion through charcoal is not an entirely satisfactory method for the treatment of hyperbilirubinemia.

Charged resins such as DOWEX IX (trademark; cholestyramine) and uncharged resins such as AMBERLITE XAD (trademark; a styrene-acrylic ester copolymer) have also been used with some success in hemoperfusion columns. Immobilized human serum albumin is a somewhat more selective adsorbent, that is also biocompatible, but its usefulness is limited severely by the fact that one molecule of human serum albumin with a molecular weight of about 66,000 binds only two molecules of bilirubin. Thus, a large amount of human serum albumin is required to remove significant amounts of bilirubin.

At the present time, none of the available adsorbents are entirely satisfactory for use in hemoperfusion or ingestion. The major limitations are lack of specificity, low adsorption capacity and poor biocompatibility. While the latter problem may be solved by coating the adsorbent, the other two remain.

It is therefore an object of the present invention to overcome the above drawbacks and to provide novel adsorbents which are biocompatible and capable of selectively adsorbing bile pigments and bile acids, and which have improved adsorption capacity.

In accordance with the invention, there is provided a novel polymer addition product comprising a hydrophilic polymer backbone having a molecular weight of at least about 5,000 and to which are attached amino acid containing pendants, the pendants containing at least one arginine or lysine amino acid.

It has been found quite unexpectedly that the above polymeric compounds are highly efficient adsorbents for bilirubin and other bile pigments, as well as for bile acids such as cholic acid. Experimental results clearly indicated a strong interaction of bilirubin with polymer resins containing either an arginine (Arg) or lysine (Lys) pendant group, but those with other amino acid pendants gave indication of only minimal sorption. By comparison, a water-swellable polyamide resin with arginine containing pendants adsorbed bilirubin efficiently with a complete monolayer capacity 35 times greater than that of the commonly used cholestyramine (DOWEX IX2).

Only arginine and lysine have been found to be active for binding bilirubin when they are present as pendants on a hydrophilic polymer backbone and, of the amino acids tested, these are the only two that have a positively charged R group at a pH of 7.8. Bilirubin is known to exist as a dianion in aqueous solution at a pH of 7.8. It is possible, therefore, that a salt linkage between the carboxylic acid groups of bilirubin and the positively charged R group of arginine and lysine is responsible for the observed interaction with bilirubin. The other amino acids are not ionized at a pH of 7.8 and, consequently, are unable to form salt linkages.

It has also been observed that the amount of bilirubin adsorbed from aqueous buffer solutions (pH=7.8) by the compounds of the invention increases with increasing basicity of the amino acids in the pendants. As the number of basic amino acids in the pendant is increased from one to five a 4.7 fold enhancement in the adsorption capacity is seen for arginine while a 9.3 fold enhancement is obtained for lysine.

The polymer addition products according to the invention preferably have the following general formula:

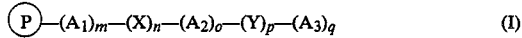

wherein:
the symbol (P)— represents the polymer backbone; $A_1$, $A_2$ and $A_3$ are identical or different and each represent an amino acid or an oligo-peptidic chain; X and Y are identical or different and each represent Arg or Lys, or a sequence thereof; and m, n, o, p and q are, independently, 0 or 1; with the proviso that at least one of n and p is 1 and the total number of amino acids in any pendant does not exceed about 20.

The polymer backbone onto which the amino acid or peptide pendants are attached must be hydrophilic so as to swell in an aqueous medium. This ensures good contact with the medium and also opens the pores in the polymer so that there is good access to all of the active pendants. The minimum molecular weight should be at least about 5,000 to prevent passage through the walls of the gastrointestinal tract. The polymer preferably has a molecular weight in the range of from about 5,000 to about 2,000,000. It can be either linear or crosslinked, but is preferably cross-linked so as to be insoluble in the blood plasma when using the hemoperfusion method of treatment. The polymer backbone must of course also contain appropriate functional groups so that the desired amino acid or peptide pendants can be attached thereto.

The polymer addition products of the invention are thus biocompatible since, as stated above, the polymer backbone is either of large molecular weight (>5,000) so that, in the ingestion method, it will not pass through the walls of the gastrointestinal tract or else it is cross-linked so that, in the hemoperfusion method, it will not dissolve in the blood plasma. On the other hand, the pendants are composed of amino acids known to be biocompatible.

A preferred polymer resin for use as backbone onto which the pendants can be synthesized is a polyamide resin available from Chemalog under catalogue No. 74-3660-00, which is a water swellable copolymer of dimethylacrylamide and N-acryl-1,6-diaminohexane reticulated with bisacrylyldiaminoethane. It is sold as a hydrochloride salt. The first amino acid of the pendants can be attached directly to resin $NH_2$ groups, following neutralization, via the amino acid COOH group, thus forming an amide bond. A trialanine ($Ala_3$) or other nonbasic amino acid portion acting as spacer is preferably included next to the polymer backbone to extend the active Arg or Lys unit away from the backbone so as to make it more accessible for sorption.

Thus, a particularly preferred polymer addition product according to the invention may be represented by the following formula:

wherein Z is Arg or Lys, and r is an integer varying from 1 to 5.

Doubling the number of active amino acids in the pendant generally results in an increased adsorption capacity for bilirubin. This suggests that charge density is an important factor in the adsorption of bilirubin by the compounds of the invention. In the case of arginine, increasing the number of charged amino acids from two to three has no apparent effect on the adsorption capacity for bilirubin, but a further increase to five enhances the adsorption capacity by a factor of 4.7 as compared to that of the resin with pendants containing only one amino acid. For lysine, the adsorption is enhanced by a factor of 9.3 when the pendant length is increased from one to five Lys units.

It is of interest to note that although a resin with $Arg_2Ala_3$ pendants has a greater adsorption capacity for bilirubin per equivalent than does a $Lys_2Ala_3$ containing resin, the capacity of a $Arg_5Ala_3$ containing resin is somewhat less than that of the $Lys_5Ala_3$ containing resin. Apparently, there is an optimum in charge density so that a further increase in basicity is not reflected in a larger adsorption capacity. Rather surprisingly, resins with $Arg_2Ala_3$ and $Arg_3Ala_3$ pendants have approximately an equal capacity for bilirubin which suggests that factors other than charge density, perhaps conformation of the peptide chain, also play a significant role in the adsorption process.

The effect of the length of the pendants as opposed to its charge density was tested using arginine containing resins with extra alanine spacers either at the beginning of the chain, i.e., before the first arginine, or between arginines. Each of these resins can be related to another resin with either the same number of amino acids or with the same number of arginines in the pendant. The $Arg_1Ala_4$ pendant behaves like $Arg_1Ala_3$ which has the same number of arginines rather than like $Arg_2Ala_3$ which has the same number of amino acids in the pendants. Similarly, $Arg_1Ala_3Arg_1Ala_3$ pendants behave like $Arg_2Ala_3$ and not like $Arg_5Ala_3$. The $Ala_3$ spacer separating the arginines apparently has minimal effect on the adsorption capacity that seems to be more dependant on the number of arginines in the pendants than on the length of the pendants.

Where a polyamide resin is used as the polymer backbone, the amino containing acid pendants can be synthesized onto such a resin by first preparing an anhydride of N and side chain protected amino acid, coupling the anhydride to the polyamide resin, then deprotecting the amino acid at the N group and stepwise coupling N and side chain protected amino acids to form a resin-coupled peptide, wherein at least one of the amino acids coupled is arginine or lysine. The resin-coupled peptide is thereafter completely deprotected.

The synthesis of peptide pendants on a polymer backbone is advantageously effected by solid phase peptide synthesis which can be achieved using an automatic solid phase peptide synthesizer, such as the Vega model 250 peptide synthesizer. The solid phase synthesis of peptides is extensively described by John M. Stewart and Janis D. Young in "Solid Phase Peptide Synthesis", Pierce Chem. Corp., Rockford, Ill., 1984. Stewart and Young describe the chemistry of solid phase peptide synthesis, laboratory techniques and apparatus and the book includes extensive appendices on apparatus, chemicals and reagents, amino acids, protecting groups and reagents, to which reference can be made for a more complete understanding of the present invention.

As mentioned previously, the compounds of the invention are useful in the treatment of hyperbilirubinemia by adsorption of bilirubin from blood plasma or from the gastrointestinal tract. Although bilirubin was the only bile pigment tested, it is expected that these compounds will also adsorb other bile pigments such as biliverdin, mesobiliverdin, mesobilirhodin, mesobilirubin, urobilin-I and urobilin-L, which are structurally similar to bilirubin.

The compounds of the invention have also been found to adsorb cholic acid which is a bile acid. Other bile acids such as chenodeoxycholic acid, lithocholic acid, deoxycholic acid, taurocholic acid and glycocholic acid are expected to be equally adsorbed. The significance of bile acid adsorption is related to the lowering of serum cholesterol. As it is known, cholesterol is the major and probably the sole precursor of bile acids. During normal digestion, bile acids are secreted via the bile from the liver and gallbladder into the intestines. Bile acids emulsify the fat and lipid materials present in food, thus facilitating absorption. A major portion of the bile acids secreted is reabsorbed from the intestines and returned via the portal circulation of the liver, thus completing the enterohepatic cycle. The binding of bile acids in the intestines onto an insoluble adsorbent that is excreted in the feces results in partial removal of the bile acids from the enterohepatic circulation, preventing their reabsorption. The increased fecal loss of bile acids leads to an increased oxidation of cholesterol to bile acids, a decrease in beta-lipoprotein or low density lipoprotein serum levels, and a decrease in serum cholesterol levels. Thus, the compounds of the invention can be used for reducing hypercholesteremia in affected humans.

Figure 2:
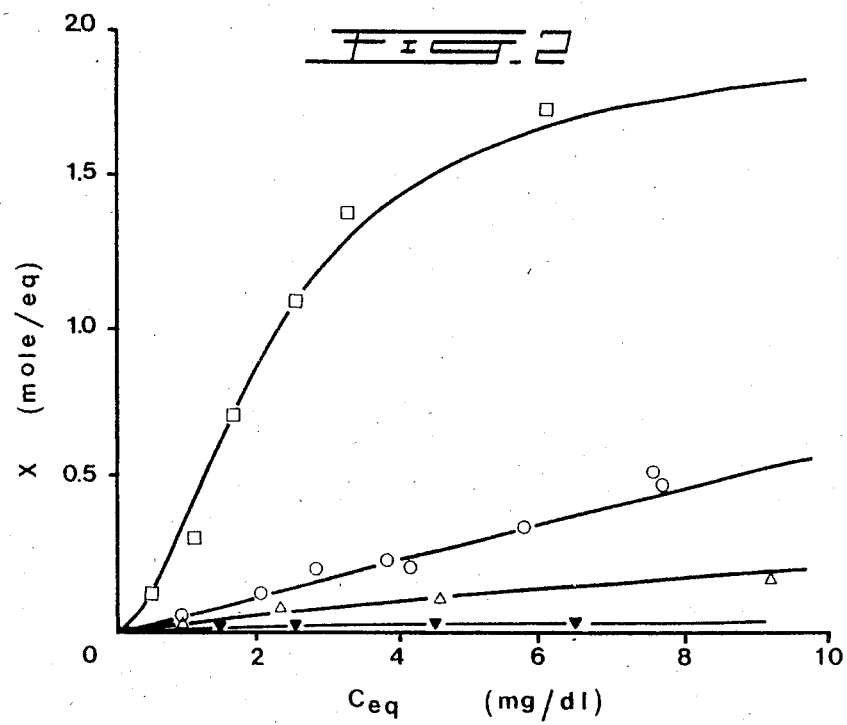

Further features and advantages of the invention will become more readily apparent from the following non-limiting examples and the accompanying drawings, in which:

FIGS. 1 and 2 show the absorption isotherms of compounds according to the invention for bilirubin, compared with the adsorption isotherm of cholestyramine (used as reference adsorbent).

1. Preparation of Polyamide Peptide Resins

A water swellable polyamide resin available from Chemalog (Chemical Dynamics Corporation, P.O. Box 395, 3001 Hadley Road, South Plainfield, N.J. 07080, U.S.A.) under catalogue No. 74-3660-00, which consists of poly(dimethylacrylamide-co-N,N'-bisacrylyl-1,2-diaminoethane-co-N-acryl-1,6-diaminohexane.HCl), 11% crosslinked, was used as the polymer backbone onto which the peptide pendants were synthesized.

The synthesis of the peptide pendants onto the polyamide resin was achieved on a Vega model 250 automatic peptide synthesizer by the symmetrical anhydride method according to the schedule shown in the following Table.

TABLE 1

PROGRAM FOR AUTOMATED SOLID PHASE PEPTIDE SYNTHESIS

| Step | Operation | Reagent | Number of repetitions | Time (minutes) |
|---|---|---|---|---|
| 1 | coupling | symmetrical anhydride | 1 | until completion |
| 2 | washing | $CH_2Cl_2$ | 2 | 1 |
| 3 | washing | DMF | 1 | 1 |
| 4 | washing | $CH_2Cl_2$ | 3 | 1 |
| 5 | deprotection | 40% TFA in $CH_2Cl_2$ | 1 | 20 |
| 6 | washing | $CH_2Cl_2$ | 2 | 1 |
| 7 | washing | dioxane/$CH_2Cl_2$ | 2 | 1 |
| 8 | washing | $CH_2Cl_2$ | 2 | 1 |
| 9 | washing | DMF | 2 | 1 |
| 10 | washing | 5% DEA in $CH_2Cl_2$ | 2 | 0.75 |
| 11 | neutralization | 5% DEA in $CH_2Cl_2$ | 1 | 5 |
| 12 | washing | $CH_2Cl_2$ | 4 | 2 |
| 13 | next coupling back to step 1 | | | |

The polyamide resin was first swollen in dichloromethane and the hydrochloride salt was displaced with 40% diisopropylethylamine (DEA) in dichloromethane (30 minutes). Fully protected amino acids, N-$\alpha$-t-BOC-L-alanine, N-$\alpha$-t-Boc-2-bromo-Cbz-L-tyrosine, N-$\alpha$-t-Boc-N-$\epsilon$-2,4-dichloro-Cbz-L-lysine, N-$\alpha$-t-Boc-N-imtosyl-L-histidine and N-$\alpha$-t-Boc-N-w-nitro-L-arginine were obtained from Chemalog. The symmetrical anhydrides of the amino acids used as the active intermediates in the coupling step were obtained by mixing a solution of two equivalents of the amino acid in dichloromethane or tetrahydrofuran (for arginine) with one equivalent of N,N'-dicyclohexylcarbodiimide (DCC) (10% in $CH_2Cl_2$). The reaction occurred at 0° C. for 20 minutes. Upon completion of the reaction, the dicyclohexyl urea, obtained as a by-product, was filtered off and the filtrate containing the reactive intermediate was added to the resin.

Upon completion of the coupling step the $\alpha$-amino groups were deprotected with 40% trifluoroacetic acid (TFA), neutralized with 5% DEA and washed. The next amino acid was added and the synthesis sequence was repeated. Completion of each coupling step and deprotection of the $\alpha$-amino groups were checked with the ninhydrin test which can detect less than 1% of free $NH_2$ so that a minimum of 99% completion of each coupling step is indicated.

The sorbents were synthesized in different batches. To obtain the various pendant lengths in a given bath, part of the resin was withdrawn when a given sequence length was complete. The synthesis was resumed with the remaining sample. After the last amino acid in the sequence had been introduced, deprotected, neutralized and washed, the resin was washed a last time with anhydrous ethyl ether and dried overnight under vacuum.

The R groups were then deprotected by treatment with anhydrous HF. The resin was introduced into a reaction flask, one ml of anisol was added and the flask was securely screwed into a HF line. The reaction mixture was cooled with liquid $N_2$ and HF (15–20 ml per gram of resin) was distilled in the reaction flask. The mixture was warmed to 0° C. while the resin was stirred with a magnetic stirrer to ensure the complete penetration of the resin by HF. Once the HF had melted, the stirring was kept to a minimum to avoid grinding the resin. After one hour the HF was evaporated, the resin was washed with anhydrous ethyl ether, dried under vacuum and kept in a vacuum dessicator until use.

2. Adsorption studies

Solutions of bilirubin were prepared daily by dissolving bilirubin powder (from bovine gallstones, Sigma) in 0.010M NaOH and adjusting the volume with KH$_2$PO$_4$ buffer to achieve a final pH of 7.8±0.1 and a concentration of 10.0 mg/dl. This stock solution was diluted with KH$_2$PO$_4$/NaOH buffer (pH=7.8) as required. The solutions were kept in the dark at 0° C. and all experiments were made in a dark room using a red light.

The adsorption was initiated by adding 25 ml of bilirubin solution at an appropriate concentration to approximately 10 mg of polyamide resin contained in an adsorption flask. The flask was placed in an ice water bath and purged continuously with nitrogen. An aliquot was taken for analysis at 60 minutes. Duplicate experiments were reproducible to ±5%.

The concentration of bilirubin was determined from the adsorbance at 438 nm measured with a Beckmann model 25 double beam spectrophotometer using the buffer solution as the reference. Calibration experiments with bilirubin solutions of known concentration yielded a linear Beer's law plot, in the concentration range of these studies, with a molar extinction coefficient of $4.44 \times 10^{-4}$ 1 mol$^{-1}$ cm$^{-1}$.

EXAMPLE 1

A polyamide peptide resin was prepared as described above by grafting onto the polyamide backbone three alanine fragments followed by one arginine. The resin (5-10 mg) was stirred with a bilirubin solution (1-10 mg/dl) for one hour. The amount of bilirubin adsorbed was measured by the diminution in adsorbance at 438 nm. At an equilibrium concentration of 6 mg/dl, this resin adsorbed 39 mg of bilirubin per gram of resin.

EXAMPLE 2

Example 1 was repeated except that four alanines instead of three were grafted onto the polyamide backbone, followed by one arginine. The amount of bilirubin adsorbed by the resin thus obtained, as measured spectrophotometrically, was 36 mg of bilirubin per gram of resin at an equilibrium concentration of 6 mg/dl.

EXAMPLE 3

Example 1 was repeated except that the number of active arginine units in the pendants was doubled. The amount of bilirubin adsorbed by the resin thus obtained, as measured spectrophotometrically, was 131 mg of bilirubin per gram of resin at an equilibrium concentration of 6 mg/dl.

The adsorption capacity of this resin for cholic acid was also tested, according to the procedure described by Boyd, Eastwood and Maclean in *J. Lipid Research*, Vol. 7, page 83 (1966). The resin (10 mg) was stirred with a solution of cholic acid (10 mg/dl) for one hour. At an equilibrium concentration of 5 mg/dl, the amount of cholic acid adsorbed by the resin, as measured spectrophotometrically (510 nm), was 137 mg of cholic acid per gram of resin.

EXAMPLE 4

Example 3 was repeated except that one histidine was coupled to the terminal arginine of the peptide pendants. The amount of bilirubin adsorbed by the resin thus obtained, as measured spectrophotometrically, was 133 mg of bilirubin per gram of resin at an equilibrium concentration of 6 mg/dl.

Histidine thus improves the adsorption capacity of a resin with Arg$_2$Ala$_3$ pendants.

EXAMPLE 5

Example 1 was repeated except that a trialanine spacer was coupled to the arginine of the peptidic pendants, followed by one arginine. The amount of bilirubin adsorbed by the resin thus obtained, as measured spectrophotometrically, was 140 mg per gram of resin at an equilibrium concentration of 6 mg/dl.

EXAMPLE 6

Example 1 was repeated except that the number of active arginine units in the pendants was increased to three. The amount of bilirubin adsorbed by the resin thus obtained, as measured spectrophotometrically, was 131 mg per gram of resin at an equilibrium concentration of 6 mg/dl.

EXAMPLE 7

Example 1 was repeated except that the number of active arginine units in the pendants was increased to five. The amount of bilirubin adsorbed by the resin thus obtained, as measured spectrophotometrically, was 157 mg of bilirubin per gram of resin at an equilibrium concentration of 6 mg/dl.

EXAMPLE 8

Example 1 was repeated except that the arginine was replaced by lysine. The amount of bilirubin adsorbed by the resin thus obtained, as measured spectrophotometrically, was 17 mg of bilirubin per gram of resin at an equilibrium concentration of 6 mg/dl.

EXAMPLE 9

Example 8 was repeated except that the number of active lysine units in the pendants was doubled. The amount of bilirubin adsorbed by the resin thus obtained, as measured spectrophotometrically, was 41 mg of biluribin per gram of resin at an equilibrium concentration of 6 mg/dl.

EXAMPLE 10

Example 8 was repeated except that the number of active lysine units in the pendants was increased to five. The amount of bilirubin adsorbed by the resin thus obtained, as measured spectrophotometrically, was 181 mg of bilirubin per gram of resin at an equilibrium concentration of 6 mg/dl.

The adsorption capacities of the polyamide peptide resins prepared in Examples 1 through 10 are summarized in the following Table:

TABLE 2

| Ex. No. | Formula | Adsorption Capacity* |
|---|---|---|
| 1 | Arg$_1$Ala$_3$—Polyamide | 0.32 |
| 2 | Arg$_1$Ala$_4$—Polyamide | 0.30 |
| 3 | Arg$_2$Ala$_3$—Polyamide | 1.12 |
| 4 | His$_1$Arg$_2$Ala$_3$—Polyamide | 1.17 |
| 5 | Arg$_1$Ala$_3$Arg$_1$Ala$_3$—Polyamide | 1.26 |
| 6 | Arg$_3$Ala$_3$—Polyamide | 1.15 |
| 7 | Arg$_5$Ala$_3$—Polyamide | 1.47 |
| 8 | Lys$_1$Ala$_3$—Polyamide | 0.14 |
| 9 | Lys$_2$Ala$_3$—Polyamide | 0.35 |
| 10 | Lys$_5$Ala$_3$—Polyamide | 1.65 |

*Equivalents of bilirubin adsorbed per equivalents of pendants (at an equilibrium concentration of 6 mg/dl).

The adsorption isotherms of the resins of Examples 1, 3, 6 and 7 for bilirubin are reported in FIG. 1, in which:

Δ: Arg$_1$Ala$_3$—Polyamide

○: Arg$_2$Ala$_3$—Polyamide
∇: Arg$_3$Ala$_3$—Polyamide
□: Arg$_5$Ala$_3$—Polyamide
▼: Cholestyramine (reference adsorbent).

On the other hand, the adsorption isotherms of the resins of Examples 8, 9 and 10 for bilirubin are reported in FIG. 2, in which:

△: Lys$_1$Ala$_3$—Polyamide
▼: Lys$_2$Ala$_3$—Polyamide
□: Lys$_5$Ala$_3$—Polyamide
▼: Cholestyramine (reference adsorbent).

As it is apparent, the polyamide peptide resins according to the invention have a much greater adsorption capacity for bilirubin than the commonly used cholestyramine.

The following additional experiments were carried out to ascertain whether polyamide peptide resins with pendants containing amino acids other than arginine or lysine would be effective in adsorbing bilirubin.

COMPARATIVE EXAMPLE 1

A polyamide peptide resin was prepared as described earlier by grafting onto the polyamide backbone three alanines, followed by one tyrosine. The resin thus obtained was tested for its adsorption capacity for bilirubin and gave indication of only minimal sorption.

COMPARATIVE EXAMPLE 2

Comparative Example 1 was repeated except that the tyrosine was replaced by histidine. The resin thus obtained was tested for its adsorption capacity for bilirubin and gave indication of only minimal sorption.

COMPARATIVE EXAMPLE 3

Comparative Example 1 was repeated except that the number of tyrosine units in the pendants was doubled. The resin thus obtained was tested for its adsorption capacity for bilirubin and gave indication of only minimal sorption.

We claim:

1. A polymer addition product comprising a hydrophilic polymer backbone having a molecular weight of at least about 5,000 and to which are chemically bonded amino acid containing pendants, said pendants containing at least one arginine or lysine amino acid in deprotected form.

2. A polymer addition product as claimed in claim 1, wherein said polymer backbone has a molecular weight of from about 5,000 to about 2,000,000.

3. A polymer addition product as claimed in claim 1, wherein said polymer backbone is cross-linked.

4. A polymer addition product as claimed in claim 1, having the general formula:

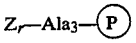—(A$_1$)$_m$—(X)$_n$—(A$_2$)$_o$—(Y)$_p$—(A$_3$)$_q$     (I)

wherein:
the symbol 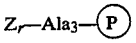— represents the polymer backbone;
A$_1$, A$_2$ and A$_3$ are identical or different and each represent an amino acid or an oligo-peptidic chain;
X and Y are identical or different and each represent Arg or Lys, or a sequence thereof; and
m, n, o, p and q are, independently, 0 or 1; with the proviso that at least one of n and p is 1 and the total number of amino acids in any pendant does not exceed about 20.

5. A polymer addition product as claimed in claim 4, having the formula:

Z$_r$—Ala$_3$—     (I')

wherein — represents a water swellable polyamide resin, Z is Arg or Lys and r is an integer varying from 1 to 5.

6. A polymer addition product as claimed in claim 5, wherein said water swellable polyamide resin is a copolymer of dimethylacrylamide and N-acryl-1,6-diaminohexane reticulated with bisacrylyldiaminoethane.

7. A polymer addition product as claimed in claim 5, wherein — represents a water swellable copolymer of dimethylacrylamide and N-acryl-1,6-diaminohexane reticulated with bisacrylyldiaminoethane, Z is Arg and n is 2.

8. A polymer addition product as claimed in claim 5, wherein — represents a water swellable copolymer of dimethylacrylamide and N-acryl-1,6-diaminohexane reticulated with bisacrylyldiaminoethane, Z is Arg and n is 3.

9. A polymer addition product as claimed in claim 5, wherein — represents a water swellable copolymer of dimethylacrylamide and N-acryl-1,6-diaminohexane reticulated with bisacrylyldiaminoethane, Z is Arg and n is 5.

10. A polymer addition product as claimed in claim 5, wherein — represents a water swellable copolymer of dimethylacrylamide and N-acryl-1,6-diaminohexane reticulated with bisacrylyldiaminoethane, Z is Lys and n is 5.

11. A polymer addition product as claimed in claim 4, having the formula:

His$_1$Arg$_2$Ala$_3$—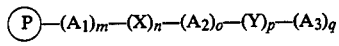

wherein — represents a water swellable copolymer of dimethylacrylamide and N-acryl-1,6-diaminohexane reticulated with bisacrylyldiaminoethane.

12. A polymer addition product as claimed in claim 4, having the formula:

Arg$_1$Ala$_3$Arg$_1$Ala$_3$—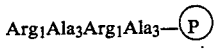

wherein 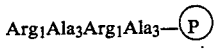— represents a water swellable copolymer of dimethylacrylamide and N-acryl-1,6-diaminohexane reticulated with bisacrylyldiaminoethane.

13. A method of treating hyperbilirubinemia in an affected human, which comprises orally administering to said human an effective bilirubin-adsorbing amount of a polymer addition product as defined in claim 1.

14. A method as claimed in claim 13, wherein the polymer addition product has the formula:

Z$_r$—Ala$_3$—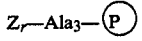     (I')

wherein 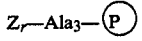— represents a water swellable polyamide resin, Z is Arg or Lys and r is an integer varying from 1 to 5.

15. A method as claimed in claim 14, wherein the water swellable polyamide resin is a copolymer of dimethylacrylamide and N-acryl-1,6-diaminohexane reticulated with bisacrylyldiaminoethane.

16. A method of treating hyperbilirubinemia in an affected human by hemoperfusion, which comprises perfusing blood plasma from said human through a column packed with a bilirubin adsorbent consisting of a polymer addition product as defined in claim 1.

17. A method as claimed in claim 16, wherein the polymer addition product has the formula:

$$Z_r\text{—Ala}_3\text{—}\textcircled{P} \qquad (I')$$

wherein $\textcircled{P}$— represents a water swellable polyamide resin, Z is Arg or Lys and r is an integer varying from 1 to 5.

18. A method as claimed in claim 17, wherein the water swellable polyamide resin is a copolymer of dimethylacrylamide and N-acryl-1,6-diaminohexane reticulated with bisacrylyldiaminoethane.

19. A method of reducing hypercholesteremia in an affected human, which comprises orally administering to said human an effective bile acid-adsorbing amount of a polymer addition product as defined in claim 1.

20. A method as claimed in claim 19, wherein the polymer addition product has the formula:

$$Z_r\text{—Ala}_3\text{—}\textcircled{P} \qquad (I')$$

wherein $\textcircled{P}$— represents a water swellable polyamide resin, Z is Arg or Lys and r is an integer varying from 1 to 5.

* * * * *

UNITED STATES PATENT AND TRADEMARK OFFICE
CERTIFICATE OF CORRECTION

PATENT NO. : 4,593,073
DATED : June 3, 1986
INVENTOR(S) : St.-Pierre, Leon E.

It is certified that error appears in the above-identified patent and that said Letters Patent is hereby corrected as shown below:

-- The Assignee's information has been spelled incorrectly on the Letters Patent. It should read as follows:

THE ROYAL INSTITUTION FOR THE ADVANCEMENT OF LEARNING (McGILL Univ.), CANADA --

Signed and Sealed this

Nineteenth Day of August 1986

[SEAL]

Attest:

Attesting Officer

DONALD J. QUIGG

Commissioner of Patents and Trademarks